United States Patent
Bransby

(10) Patent No.: US 6,389,746 B1
(45) Date of Patent: May 21, 2002

(54) METHOD OF PROPAGATING FIBERCANE (ARUNDO)

(76) Inventor: David I. Bransby, 2668 Wire Rd., Auburn, AL (US) 36832

( * ) Notice: Subject to any disclaimer, the term of this patent is extended or adjusted under 35 U.S.C. 154(b) by 0 days.

(21) Appl. No.: 09/417,001

(22) Filed: Oct. 12, 1999

(51) Int. Cl.$^7$ ................................................ A01G 1/00
(52) U.S. Cl. .................................................. 47/58.1 R
(58) Field of Search ............................ 47/58.1; 800/320

(56) References Cited

U.S. PATENT DOCUMENTS 3,821,864 A * 7/1974 Stottlemyer ................. 47/58.1

FOREIGN PATENT DOCUMENTS

| JP | 02000135025 A | * | 5/2000 |
| SU | 536770 A | * | 12/1976 |
| WO | WO-03934 | * | 7/1986 |

OTHER PUBLICATIONS

Translation of relevant section of previously supplied article by Uhlen, R., et al., "La Canne de Provence," May, 1975, *Bulletin Technique d'Information*, No. 299 (1 page translation, plus 1 page from previously supplied article showing where translation is taken).

Bell, Gary P., *Plant Invasions: Studies from North America and Europe*, "Ecology and Management of *Arundo Donax*, and Approaches to Riparian Habitat Restoration in Southern California," 1997, pp. 103–113, Edited by J.H. Brock, et al., Backhuys Publishers, Leiden, The Netherlands.

Tracy, James L., et al., "Suitability of Classical Biological Control for Giant Reed (*Arundo Donax*) in the United States," 1999, pp. 73–109, In C.E. Bell (ed). Arundo and Saltcedar: The Deadly Duo, Proceedings of the Arundo and Saltcedar Workshop, Jun. 17, 1998, Ontario, California. Univ. of California Cooperative Extension, Holtville, California.

Perdue, Robert E., Jr., *Arundo donax*: Source of Musical Reeds and Industrial Cellulose,1958, 25 pgs. on website: http://wuarchive.wustl.edu/doc/misc/org/doublereeds/general/cane.html.

BioBase: The Giant Reed (*Arundo donax* L.) Network. Results of the first year. Contacts: Myrsini Christou and Michael Mardikis. On website: http://www.eeci.net/. (9 pages).

Uhlen, R., et al., "La Canne de Provence," May, 1975, *Bulletin Technique d'Information*, No. 299.

* cited by examiner

*Primary Examiner*—Peter M. Poon
*Assistant Examiner*—Jeffrey L. Gellner
(74) *Attorney, Agent, or Firm*—Rothwell, Figg, Ernst & Manbeck

(57) ABSTRACT

A method of propagating Arundo is disclosed. The invention relates to Arundo plants, stems and nodes and to methods of propagating new Arundo plants by using stem material as seed cane.

27 Claims, No Drawings

METHOD OF PROPAGATING FIBERCANE (ARUNDO)

BACKGROUND OF THE INVENTION

The present invention relates to fibercane (*Arundo donax* L.) and to methods of propagating new plants. *Arundo donax* is a member of the Poaceae family and has several common names including "giant reed", "Spanish cane", "giant cane", and "fibercane". Arundo is a native of Mediterranean coastal areas where it is a robust perennial grass 3 to 10 meters (9 to 30 feet) tall, growing in many-stemmed cane-like clumps. Arundo spreads from horizontal rootstocks below the soil and often forms large colonies many meters across. Individual stems or culms are tough and hollow, divided by partitions at nodes like bamboo. Stems are from 1 to 4 centimeters in diameter. Culms are unbranched or with single (rarely multiple) lateral branches from nodes. The pale green to blue-green leaves broadly clasp the stem with a heart-shaped base or leaf sheath, about 2–6 cm wide at the base of the blade or lamina and tapering to the tip, up to 70 cm or more in length. Leaves are arranged alternately (not opposite each other) throughout the culm, very distinctly two-ranked (in a single plane).

Arundo produces a tall, plume-like flower-head at the upper tips of stems, the flowers closely packed in a cream to brown colored cluster borne from early spring to early fall, but these flowers do not produce viable seeds or achenes in North America. Culms may remain green throughout the year but often fade with semi-dormancy during the winter months or in drought. Arundo can be confused with cultivated bamboos and corn, and in earlier stages with some large-stature grasses, especially Phragmites (Common reed) which is less than 4 meters tall and has panicles which are less than 3 dm with long hairs between the florets. Fibercane is a perennial reed with stems which are erect and hollow. Three species of Arundo occur world-wide in tropical to warm temperate climates. *Arundo donax* is naturalized and invasive in many regions, including southern Africa, subtropical U. S. through Mexico, the Caribbean islands and South America, Pacific Islands, Australia and Southeast Asia as described in Tracy, J. L., and DeLoach, C. J., 1999. "Suitability of Classical Biological Control for Giant Reed (*Arundo donax*) in the United States:" In C. E. Bell (ed.) Arundo and Saltcedar: The Deadly Duo, Proceedings of the Arundo and Saltcedar Workshop, Jun. 17, 1998, Ontario, Canada, pp. 73–109, and these references are incorporated herein.

Being a typical 'reed', Arundo appreciates very moist soils and will often be found growing in water at the edge of coastal 'slacks'. In its native habitat, the stems are persistent, becoming rather woody in their second year. Nodal side shoots or 'keikis' are formed along 2nd year stems and if these come into contact with the ground, will root giving rise to new plants some distance away from the parent, provided the culm is still attached to the parent plant.

Arundo is currently propagated by sections of rhizomes. The 'keikis' which readily form on second year stems also can be detached and placed in water. Rooting usually takes place within 2 or 3 weeks, after which, the young plants can be potted into 20 cm pots using a good quality compost.

The thick, woody rhizomes can also be divided in April/May before the new growths have grown too large. It is better to lift the entire rootstock and cut through the rhizomes using a very sharp knife or saw. Sections can be replanted and care should be taken to ensure that they do not dry out especially during the first few weeks.

Arundo plants in North America do not produce viable seed, and seedlings are not observed in the field. Population expansion occurs through vegetative reproduction, either from underground rhizome extension of a colony or from plant fragments carried downstream, primarily during floods, to become rooted and form new clones. Horticultural propagation in the greenhouse is routinely done by planting rhizomes which readily establish. Fresh stems form roots at nodes under laboratory conditions (T. Zimmerman and J. Bunn, unpub. data), and root formation does occur where an attached culm has fallen over and is in contact with the substrate.

New shoots arise from rhizomes in nearly any season, but are more common during spring. Growth likewise occurs in all seasons, but is highly sensitive to temperature and moisture. During warm months with ample water Arundo culms are reported to attain growth rates of 0.7 meters per week or about 4 inches per day, putting it among the fastest growing terrestrial plants. Biomass production has been estimated at 8.3 tons dry weight per acre as described in Perdue, R. E., 1958. "*Arundo donax*—source of musical reeds and industrial cellulose." *Econ. Botany*, 12(4):368–404, and which is incorporated herein. Young stems rapidly achieve the diameter of mature canes with subsequent growth involving thickening of the walls. Age of individual culms is certainly more than one year and branching seems to represent stem growth in later years, while rhizomes show indeterminant growth. Branches also form when a stem is cut or laid over. Die-back is infrequently observed but culms fade or partially brown-out during winter, apparently becoming dormant under cold conditions. The outstanding growth trait of this plant is its extremely flexible ability to survive and grow at almost any time under a wide variety of environmental conditions.

Stems are used as measuring rods, walking sticks, fishing poles, musical instruments, reeds for woodwind instruments such as clarinets and saxophones, baskets and mats. Stems also serve as support for vines and similar climbing plants, and for making trellises and the like for climbing cultivated plants. The plant makes a good quality of paper, and in Italy the plant is used in the manufacture of rayon. Variegated and glaucous-leaved varieties are used as ornamentals. Because of rather high yields from natural stands, cane has been suggested for biomass for energy. As fodder, only the young leaves are browsed; the stems are woody, and the grass unpalatable in later stages.

*Arundo donax* does not produce viable seed. Current methods of propagating Arundo involve the labor intensive process of digging up the rhizome, cutting the rhizome into sections, and then planting the rhizome sections in the field. A simpler, less labor intensive method would improve the commercial production of Arundo.

SUMMARY OF THE INVENTION

In the method of the present invention, stems of fibercane are cut above ground and laid whole or in sections in shallow furrows or on level ground. The cut stems then may remain uncovered, or are covered either partially or entirely with soil. The stems are covered by hand or with machinery. Under optimal growing conditions nodal or axillary buds will develop into plants and initiate the production of rhizomes and new plants.

DETAILED DESCRIPTION OF THE INVENTION

Definitions

In the description and tables which follow, a number of terms are used. In order to provide a clear and consistent understanding of the specification and claims, including the scope to be given such terms, the following definitions are provided:

Organic material(s) As used herein, the term 'organic material' means carbon-based material having plant, microbial or animal origin. Examples of organic materials include mulch, peat, manure, moss, bark and sawdust.

Inorganic material(s) As used herein, the term 'inorganic material' means any material that is not organic material, such as soil, limestone, ash, lime or industrial waste.

Furrow As used herein, the term 'furrow' means an extended indentation in the surface of the soil or planting medium.

Rhizome As used herein, the term 'rhizome' refers to an underground, modified, creeping stem which is solid and usually grows horizontal to the soil surface.

Node(s) As used herein, the term 'node' refers to a joint or notch on the stem or culm at which point a leaf can be attached and above which a single nodal bud is present.

Seed cane As used herein, the term 'seed cane' refers to whole stems or culms, or any portions thereof, which are used as planting material to generate new plants.

In the method of the present invention, stems of fibercane are cut above ground and laid whole or in sections in shallow furrows or on level ground. The stems then may remain uncovered, or can be covered partially or entirely with soil. The covering of the stems is done by hand or with machinery. Under optimal growing conditions nodal or axillary buds will develop into plants and initiate the production of rhizomes and new plants. In a preferred embodiment of the invention, the following conditions are met:

1) Seed cane having viable nodal buds, that may be dormant or starting to produce shoots, should be neither too old nor too young. In most environments, 6–9 months is usually the optimal age, but in frost-free environments, stems that are more than a year old will often result in successful establishment.

2) The seed cane should not be covered too deep in the soil; 5 cm or less is usually optimal. This can be done by hand or by machines such as sugarcane planters.

3) After planting, moisture needs to be supplied by adequate rainfall and/or supplemental irrigation.

4) Seed cane should be planted as soon as possible after harvesting, although it can be stored under cool, moist conditions for as long as several months.

There are numerous advantages of using the method of the present invention. Since *Arundo donax* does not produce viable seed, it currently is propagated commercially by using the buds on the underground rhizomes as propagules. The method of the present invention uses buds associated with the above-ground nodes on the stem or culm (seed cane) as propagules. The stems of Arundo are hollow, but the rhizomes are solid. Seed cane can be harvested by hand with hand tools, chainsaws or with other machinery such as sickle-bar mowers or disk mowers mounted on a tractor. Compared to harvesting underground rhizomes, much less time is required to harvest a given number of propagules using the method of the present invention. Also, the weight of seed cane per propagule is much less than the weight of rhizome per propagule, which makes physical handling of the propagules easier. Since seed cane is not contaminated with soil, as the rhizomes are, seed cane more easily meets phytosanitary regulations and will be easier and cheaper to import and export compared to rhizomes. Also, since harvesting seed cane does not disrupt the rhizomes underground, areas used for seed stock do not have to be replanted after harvesting seed cane and repeated generation of propagules is faster and cheaper for seed cane versus using rhizomes.

EXAMPLES

The following examples are provided to further illustrate the present invention and are not intended to limit the invention beyond the limitations set forth in the appended claims.

Example 1

Seed cane was harvested from a wild clump of fibercane growing adjacent to Highway 29 near Tuskegee in Macon County, Ala., on Oct. 21, 1998. Several hundred canes were cut at a height of approximately 15 cm above the soil, and they were stored outside in a pile at Auburn, Ala. with no protection from the weather.

An initial observational planting of 20 canes was done by hand on Dec. 12, 1998 at 2668 Wire Road, Auburn, Lee County, Ala. Unexpectedly, shoots from this planting started to emerge in February, 1999, but they were relatively sparse because only single canes had been placed end to end in the furrows. More seed cane was planted on Mar. 15, 1999, after about 5 months in the storage pile. This was done by opening a shallow furrow with a plow, placing canes end to end with 3 canes adjacent and parallel to one another, but staggered in the furrows, and covering the canes with about 5 cm of soil. The cane was planted in 12 rows which were 1 m apart and 20 m long. Therefore, excluding the two outside rows, this provided a total of 200 m of test rows. No fertilizer or weed control was applied.

On Aug. 1, 1999, ten 3-meter sections of row were randomly located and the number of primary and secondary stems in each section was recorded to determine the average number of stems per meter of row. In addition, 10 primary stems and 10 secondary stems were randomly located to determine average stem length and diameter, number of leaves per stem, leaf length and leaf width. All 10 stems were then pooled to determine moisture content of leaves and stems by weighing before and after drying in a forced air oven at 60° C. to constant weight. Leaf to stem ratio was determined on a dry matter basis. Growth rate of secondary stems over a 3-week period was determined by measuring the height (from the ground to the highest fully exposed leaf collar) of 16 randomly located stems on Jul. 5 and 26, 1999.

A propagule harvesting test was also conducted on Aug. 1, 1999, on a wild clump of fibercane on the Wire Road right-of-way just north of Interstate 85 in Macon County, Ala. It took one person 90 seconds to cut 10 stems with garden loppers, and to stack them in a pile, for the purpose of comparison, one person then used a pick-axe to excavate rhizomes. The stems and rhizomes were then weighed, and the total number of propagules on each was counted.

Leaves of fibercane were also harvested and analyzed for forage quality and mineral content.

Example 2

Within two weeks, primary shoots started to emerge from the nodal buds on the seed cane planted in March, 1999 and emergence of new shoots continued for several weeks. A very important observation at this time was that the soil had crusted severely, as do many soils in the Southeast when they dry out, but the primary shoots were remarkably successful in breaking through this thick crust. Also, stems developed from the seed cane, regardless of the orientation of the plane of the nodal buds, and even if this plane was orientated vertically, with buds alternating between the top and bottom of the horizontally placed cane.

Primary stems were slender and they grew at a relatively slow rate. By late May, 1999, secondary shoots started to emerge. These were considerably larger in diameter than the primary shoots, and grew rapidly. Excavation of these plants indicated that rhizomes had started to develop, and new secondary shoots continued to emerge through Aug. 1, 1999. By this time there were 5.37 primary stems and 2.70 secondary stems per meter of row as shown in Table 1. This translated into an average space of 18.6 cm between primary stems, and 37 cm between secondary stems within rows.

TABLE 1

Number of stems per meter of row, based on ten 3-meter sections of row

|  | Stem Type | | |
| --- | --- | --- | --- |
|  | Primary | Secondary | Total |
| Mean | 5.37 | 2.70 | 8.07 |
| Range | 3.0–9.7 | 1.3–4.3 | 4.7–14.0 |
| SD* | 2.12 | 0.93 | 2.95 |
| CV %** | 40 | 35 | 37 |

*SD = Standard deviation
**CV = Coefficient of variation

Example 3

Stem width and length were greater (P>0.05) for secondary stems than for primary stems, as were leaf length and width (Table 2). There were a similar number of leaves (and therefore, nodes) per stem for the two types of stem. Because the secondary stems were longer, this resulted in longer internodes: on average these were 11.5 cm for secondary stems and 7.7 cm for primary stems.

TABLE 2

Characteristics of primary and secondary stems generated from seed cane which was planted on March 15, 1999 and measured on August 1, 1999

|  | Primary Stems | | | Secondary Stems | | |
| --- | --- | --- | --- | --- | --- | --- |
| Variable | Mean | SD* | CV %** | Mean | SD* | CV %** |
| Stem Width (mm) | 6.49 | 1.25 | 19.3 | 16.24 | 3.56 | 21.7 |
| Stem Length (m) | 1.32 | 0.17 | 13.2 | 1.79 | 0.73 | 40.8 |
| Leaves per Stem | 17.2 | 2.44 | 14.2 | 15.6 | 5.52 | 35.4 |
| Leaf Length (cm) | 52.6 | 3.24 | 6.2 | 64.2 | 13.0 | 20.3 |
| Leaf Width (mm) | 34.0 | 2.67 | 7.8 | 56.5 | 7.82 | 13.8 |
| Leaf Dry Matter % | 25.7 | | | 22.1 | | |
| Stem Dry Matter % | 36.3 | | | 22.9 | | |
| Whole Plant DM % | 31.0 | | | 22.7 | | |
| Leaf:Stem Ratio | 42:58 | | | 30:70 | | |
| Total Wet Weight Leaf + Stem (g) | 66 | | | 290 | | |
| Total Dry Weight Leaf + Stem (g) | 19 | | | 61 | | |

*SD = Standard deviation
**CV = Coefficient of variation

Dry matter content was slightly higher for primary stems than for secondary stems, and primary stems had relatively more leaf material as shown in Table 2. When wet, secondary stems were 4.39 times heavier than primary stems, and when dry they were 3.2 times heavier.

Stem diameter of the new secondary shoots continued to increase, as indicated by the negative regression relationship between stem height (from ground level to the collar of the highest leaf with a fully emerged blade) and stem diameter, measured on 10 randomly located stems on Aug. 1, 1999 ($y=23.35-3.88x$; $r=0.80$, $P<0.01$, where y is stem diameter in millimeters, x is stem length in meters and r is the correlation coefficient).

Example 4

The stem extension growth rate of 16 randomly located secondary stems for the 3-week period between Jul. 5 and 26, 1999, was 6.22 cm/day (SD=1.23; CV%=19.8). Clearly, this indicates that the shorter (and therefore, younger) stems were thicker than the older or taller secondary stems.

Ten stems were cut and stacked in 90 seconds. These stems had an average of 36.7 mature leaves (SD=3.27; CV%=8.9). Since each leaf arises from a node which is associated with a nodal bud or propagule, this means that 367 propagules were harvested in 90 seconds. In contrast, the rhizomes that were harvested with a pick-axe in 90 seconds had only 8 buds or propagules. The wet weight of the ten stems was 4.58 kg, while that of the rhizomes was 1.50 kg. Consequently, weight per propagule for stem material was 4.58/367=0.0125 kg, or 12.5 g, and 1.5/8=0.187 kg, or 187 g for rhizome material, which is nearly 15 times greater. Also, it took 90/8=11.25 seconds per propagule to harvest rhizomes, but only 90/367=0.25 seconds per propagule to harvest seed cane. This indicates that the present invention is 11.25/0.25=45 times more efficient in terms of harvesting planting material, compared to the traditional method of using rhizomes.

Example 5

Rhizomes or seed cane are planted in widely spaced (10–30 feet apart) rows. After several months this results in widely spaced rows of primary and secondary stems. These stems are then used as seed cane. However, instead of cutting them off the parent plants, the stems remain attached to the parent plant, but are bent over at an angle of greater than 0 degrees to the original row so that they touch the ground, or they may be pegged to the ground. This seed cane which remains attached to the parent plant can have a portion of the top of the plant cut off and removed. They may then also be partially or completely covered with soil, organic material, or inorganic material. This results in the generation of new plants from the bent over seed cane that fills in the space between the original widely spaced rows.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A method of propagating Arundo plants comprising:
   a) cutting cane stems having one or more nodal buds to produce seed cane;
   b) planting seed cane; and
   c) harvesting growth from said seed cane without a transplanting step.

2. The method of claim 1, wherein said seed cane is covered at least partially with organic or inorganic materials.

3. The method of claim 1, wherein said seed cane is covered at least partially with soil.

4. The method of claim 1, wherein said seed cane has 1 or 2 nodes.

5. The method of claim 1, wherein said seed cane has more than 2 nodes.

6. The method of claim 1, wherein said seed cane is cut into segments having one or more nodes.

7. The method of claim 1, wherein said seed cane has at least part of a rhizome attached to the seed cane.

8. The method of claim 1, wherein said seed cane is planted within 24 hours after cutting the cane stems.

9. The method of claim 1, wherein said seed cane is stored for more than 24 hours prior to planting.

10. The method of claim 1, wherein said seed cane is stored in water to induce the nodal buds to sprout prior to planting.

11. The method of claim 1, wherein said seed cane is stored in the ground prior to planting.

12. The method of claim 1, wherein said seed cane has one or more leaves attached.

13. The method of claim 1, wherein said seed cane does not have any leaves attached.

14. The method of claim 1, wherein said seed cane is planted horizontally to the ground.

15. The method of claim 1, wherein said seed cane is planted at an angle to the ground of greater than zero degrees.

16. The method of claim 1, wherein said seed cane can be planted in furrows.

17. The method of claim 1, wherein said seed cane can be planted on top of soil and is not covered with soil.

18. The method of claim 1, wherein said seed cane is covered with soil.

19. The method of claim 1, wherein said seed cane is covered with one or more organic materials.

20. The method of claim 1, wherein said seed cane is covered with one or more inorganic materials.

21. The method of claim 1, wherein said seed cane is covered with a mixture of one or more inorganic and organic materials.

22. The method of claim 1, wherein a top portion of said seed cane is removed.

23. The method of claim 1, wherein said seed cane is bent over to initiate sprouting of nodal buds prior to cutting the seed cane.

24. A method of propagating Arundo in a commercial field comprising bending a cane stem having one or more nodes to be in contact with soil or other growing medium, without detaching said cane from the parent plant.

25. The method of claim 24, wherein said cane stem is partially covered by soil, organic material or inorganic material.

26. The method of claim 24, wherein said cane stem is completely covered by soil, organic material, or inorganic material.

27. The method of claim 24, wherein a top portion of said cane stem is removed prior to bending said cane stem to be in contact with soil or other growing medium.

* * * * *